United States Patent [19]
Reiderman et al.

[11] Patent Number: 6,163,153
[45] Date of Patent: Dec. 19, 2000

[54] NUCLEAR MAGNETIC RESONANCE PULSE SEQUENCE FOR OPTIMIZING INSTRUMENT ELECTRICAL POWER USAGE

[75] Inventors: Arcady Reiderman; Gregory B. Itskovich, both of Houston, Tex.

[73] Assignee: Western Atlas International, Inc., Houston, Tex.

[21] Appl. No.: 09/151,871

[22] Filed: Sep. 11, 1998

[51] Int. Cl.$^7$ .............................. G01V 3/00; G01R 33/20
[52] U.S. Cl. .......................... 324/314; 324/303; 324/307
[58] Field of Search .................... 324/314, 303, 324/300–322, 307, 309, 318

[56] References Cited

U.S. PATENT DOCUMENTS

| | | | |
|---|---|---|---|
| 4,318,043 | 3/1982 | Crooks at el. ........................... | 324/309 |
| 5,212,448 | 5/1993 | Le Roux et al. ....................... | 324/309 |
| 5,451,873 | 9/1995 | Freedman et al. ..................... | 324/303 |
| 5,910,112 | 6/1999 | Judd et al. .............................. | 600/410 |
| 6,005,389 | 12/1999 | Prammer ................................ | 324/303 |

OTHER PUBLICATIONS

Anatoly V. Legchenko, and Oleg A. Shushakov; "Inversion of Surface NMR Data" Geophysics vol. 63 pp. 75–84, Feb. 1998.

*Primary Examiner*—Christine K. Oda
*Assistant Examiner*—Tiffany A. Fetzner
*Attorney, Agent, or Firm*—K. P. Sriram; D. M. Springs

[57] ABSTRACT

A method for acquiring nuclear magnetic resonance measurements of a material. The method includes inducing a static magnetic field in the material, and inducing a first radio frequency magnetic field in the material to reorient nuclear magnetic spins in the material. The first radio frequency magnetic field has an amplitude and a duration selected to reorient the nuclear magnetic spins by about 90 degrees from their alignment with the static magnetic field. A second radio frequency static magnetic field is induced in the material. Nuclear magnetic resonance signals are detected after inducing the second radio frequency magnetic field. The steps of inducing the first and second radio frequency magnetic fields and detecting signals are repeated and the detected signals are stacked. The second radio frequency magnetic field has a duration and amplitude selected to reorient the nuclear magnetic spins by an angle selected to provide the stacked signal with improved signal to noise ratio compared to a single signal wherein the selected angle is 180 degrees, while consuming the same electrical power as is used to generate the single signal having the 180 degree selected angle. In the preferred embodiment, the selected angle is in a range of about 80 to 120 degrees.

14 Claims, 7 Drawing Sheets

NUCLEAR MAGNETIC RESONANCE PULSE SEQUENCE FOR OPTIMIZING INSTRUMENT ELECTRICAL POWER USAGE

BACKGROUND OF THE INVENTION

1. Field of the Invention

The invention is related to the field of nuclear magnetic resonance ("NMR") apparatus and methods. More specifically, the invention is related to methods for conducting NMR measurements in a manner which optimizes the use of electrical power by the NMR instrument.

2. Description of the Related Art

NMR instruments adapted for well logging can be used for determining, among other things, the fractional volume of pore space and the fractional volume of mobile fluid filling the pore space of earth formations. Methods for using NMR well logging measurements for determining the fractional volume of pore space and the fractional volume of mobile fluids are described, for example, in, *Spin Echo Magnetic Resonance Logging: Porosity and Free Fluid Index Determination,* M. N. Miller et al, Society of Petroleum Engineers paper no. 20561, Richardson, Tex. (1990).

NMR well logging instruments known in the art are typically designed to make measurements corresponding to an amount of time for hydrogen nuclei present in the earth formation to realign their spin axes, and consequently their bulk magnetization, either with an externally applied static magnetic field, or perpendicularly to the magnetic field, after momentary reorientation of the nuclear spin axes. The externally applied magnetic field is typically provided by a permanent magnet disposed in the NMR instrument. The spin axes of the hydrogen nuclei in the earth formation, in the aggregate, become aligned with the static magnetic field induced in the earth formation by the permanent magnet. The NMR instrument also includes an antenna positioned near the magnet and shaped so that a pulse of radio frequency (RF) power conducted through the antenna induces a corresponding RF magnetic field in the earth formation in a direction orthogonal to the static field induced by the permanent magnet. This RF pulse (called an "A-pulse" hereafter) has a duration and amplitude selected so that the spin axes of the hydrogen nuclei generally align themselves perpendicular both to the RF magnetic field and to the static magnetic field. After the A-pulse ends, the nuclear magnetic moment of the hydrogen nuclei gradually "relax" or return to their alignment with the static magnetic field. The amount of time taken for this relaxation is related to the properties of interest of the earth formation.

Also after the A-pulse ends, the antenna is typically electrically connected to a receiver, which detects and measures voltages induced in the antenna by precessional rotation of the spin axes of the hydrogen nuclei. While the hydrogen nuclei gradually realign their spin axes with the static magnetic field, they do so at different rates because of inhomogeneities in the magnet's field and because of differences in the chemical and magnetic environment within the earth formation. Different rates of realignment of the spin axes of the hydrogen nuclei result in a rapid decrease in the voltage induced in the antenna. The rapid decrease in the induced voltage is referred to as the free induction decay (FID).

After a predetermined time period following the FID, another, longer RF pulse (called a "B-pulse" hereafter) is applied to the antenna. The B-pulse has a duration and amplitude selected to reorient the spin axes of the hydrogen nuclei in the earth formation by an axial rotation of 180 degrees from their immediately previous orientations. After the B-pulse, hydrogen nuclear spin axes that were realigning with the externally applied field at a slower rate then are positioned so that they are "ahead" of the faster realigning nuclear spin axes. This causes the faster realigning axes to be positioned "behind" the slower realigning spin axes. The faster realigning spin axes then eventually "catch up" to, and come into approximate alignment with, the slower aligning spin axes at some time after the B-pulse. As a large number of the spin axes become aligned with each other, the hydrogen nuclei again are able to induce measurable voltages in the antenna. The voltages induced as a result of realignment of the hydrogen nuclear spin axes with each other after a B-pulse is referred to as a "spin echo". The voltage induced by the spin echo is typically smaller than the original FID voltage induced after cessation of the A-pulse, because the aggregate nuclear axial alignment, and consequently the bulk magnetization, of the hydrogen nuclei at the time of the spin echo is at least partially realigned with the static magnetic field and away from the sensitive axis of the antenna. The spin echo voltage itself rapidly decays by FID as the faster aligning nuclear axes again "dephase" from the slower aligning nuclear axes.

After another period of time equal to two of the predetermined time periods between the A-pulse and the first B-pulse, another B-pulse of the same amplitude and duration as the first B-pulse can be applied to the antenna. This next B-pulse again causes the slower realigning spin axes to be positioned ahead of the faster realigning axes, and eventually another spin echo will induce voltages in the antenna. The voltages induced by this next spin echo will typically be smaller those induced by the previous spin echo.

Successive B-pulses are applied at regular time intervals to the antenna to generate successive spin echoes, each one typically having a smaller amplitude than the previous spin echo. The rate at which the peak amplitude of the spin echoes decreases is related to the properties of interest of the earth formation, such as the fractional volume of pore space or the fractional volume of mobile fluid filling the pore space. The number of spin echoes needed to determine the rate of spin echo amplitude decay is related to the properties of the earth formation. In some cases as many as 1,000 spin echoes may be needed to determine the amplitude decay corresponding to the particular formation properties of interest.

A limitation of NMR well logging instruments using the just-described RF pulse sequence is that this pulse sequence uses a very large amount of electrical power. Typically the DC power requirement for the NMR logging instruments known in the art is about 1 KW; the peak power required for effective nuclear excitation can be as high as 30 KW in each pulse. As is known in the art, a typical well logging cable has a power transmission capacity of about 1.5 KW. Using NMR pulse sequences known in the art it is impractical to increase the RF power in order to improve signal to noise or to increase the axial speed ("logging speed") at which the instrument is moved through the wellbore (the increased speed being desired by the wellbore operator to save operating time and associated costs). It is also impractical to combine NMR well logging instruments using pulse sequences known in the art with other well logging instruments because the NMR logging instrument uses nearly the entire power transmission capacity of the typical well logging cable.

SUMMARY OF THE INVENTION

The invention is a method for acquiring nuclear magnetic resonance measurements of a material. The method includes inducing a static magnetic field in the material, and inducing a first radio frequency magnetic field in the material to reorient nuclear magnetic spins in the material. The first radio frequency magnetic field has an amplitude and duration selected to reorient the nuclear magnetic spins by about 90 degrees from alignment with the static magnetic field. Then a second radio frequency magnetic field is induced in the material. Nuclear magnetic resonance signals are then detected as a result of inducing the second radio frequency magnetic field. The steps of inducing the first and second radio frequency magnetic fields, and detecting the nuclear magnetic resonance signals are repeated, and the detected signals are stacked. The second radio frequency magnetic field has a duration and amplitude selected to reorient the nuclear magnetic spins by an angle which provide the stacked signal with improved signal to noise ratio compared with a single nuclear magnetic resonance signal generated using a selected angle of 180 degrees, while consuming the same amount of electrical power as is used to generate the signal nuclear magnetic resonance signal. In the preferred embodiment, the selected angle is in a range of about 80 to 120 degrees.

The invention also provides that the stacked signal can be generated using a selected realignment ("flip") angle where the signal to noise ratio is substantially the same as that of a single nuclear magnetic resonance signal generated using a 180 degree flip angle, but where less electrical power is consumed to generate the stacked signal.

DESCRIPTION OF THE PREFERRED EMBODIMENT

A typical nuclear magnetic resonance ("NMR") instrument which can make measurements according to this invention is described, for example, in U.S. Pat. No. 5,585, 720 issued to Edwards. The instrument described in the Edwards '720 patent includes a permanent magnet for inducing a static magnetic field within the materials to be analyzed. In particular, the materials to be analyzed can include earth formations surrounding a wellbore. The instrument in the Edwards '720 patent includes an antenna coil which can be wound around the magnet, circuitry for applying pulses of radio-frequency (RF) power to the antenna coil, and circuitry for detecting voltages induced in the antenna coil as a result of nuclear magnetic resonance phenomena, particularly that of hydrogen nuclei present in the earth formations.

As is known in the art, the RF pulses applied to the antenna coil of NMR apparatus such as the one in the Edwards '720 patent typically include an initial RF pulse having a duration and amplitude which reorients the nuclear spin axes of the hydrogen nuclei in the earth formations so that they become substantially perpendicular to the direction of the static magnetic field induced by the magnet. This first RF pulse (hereafter "A-pulse") is said to induce an angular deflection of about 90 degrees in the spin axes of the hydrogen nuclei. Later in the measurement cycle known in the art, a sequence of additional RF pulses (referred to as "B-pulses"), each of these B-pulses having a duration and amplitude selected to reorient the extant nuclear spin axes by about 180 degrees, is then applied to the antenna coil. In between B-pulses, the antenna coil is connected to a receiver circuit to detect voltages induced in the antenna coil as the nuclear spin axes "rephase", an event called the pulse-echo or spin echo. The combination of A-pulse and 180 degree B-pulses is known as a Carr-Purcell-Meiboom-Gill (CPMG) sequence. As is understood by those skilled in the art, the amplitude of the induced voltages from spin rephasing (pulse-echo voltages) decreases after each successive B-pulse applied to the antenna coil. The rate at which the amplitude of the successive pulse-echo voltages decays is related to properties of the earth formations such as fractional volume of pore space and the bulk volume of mobile fluids filling the pore space, as is known in the art.

Figure 1:
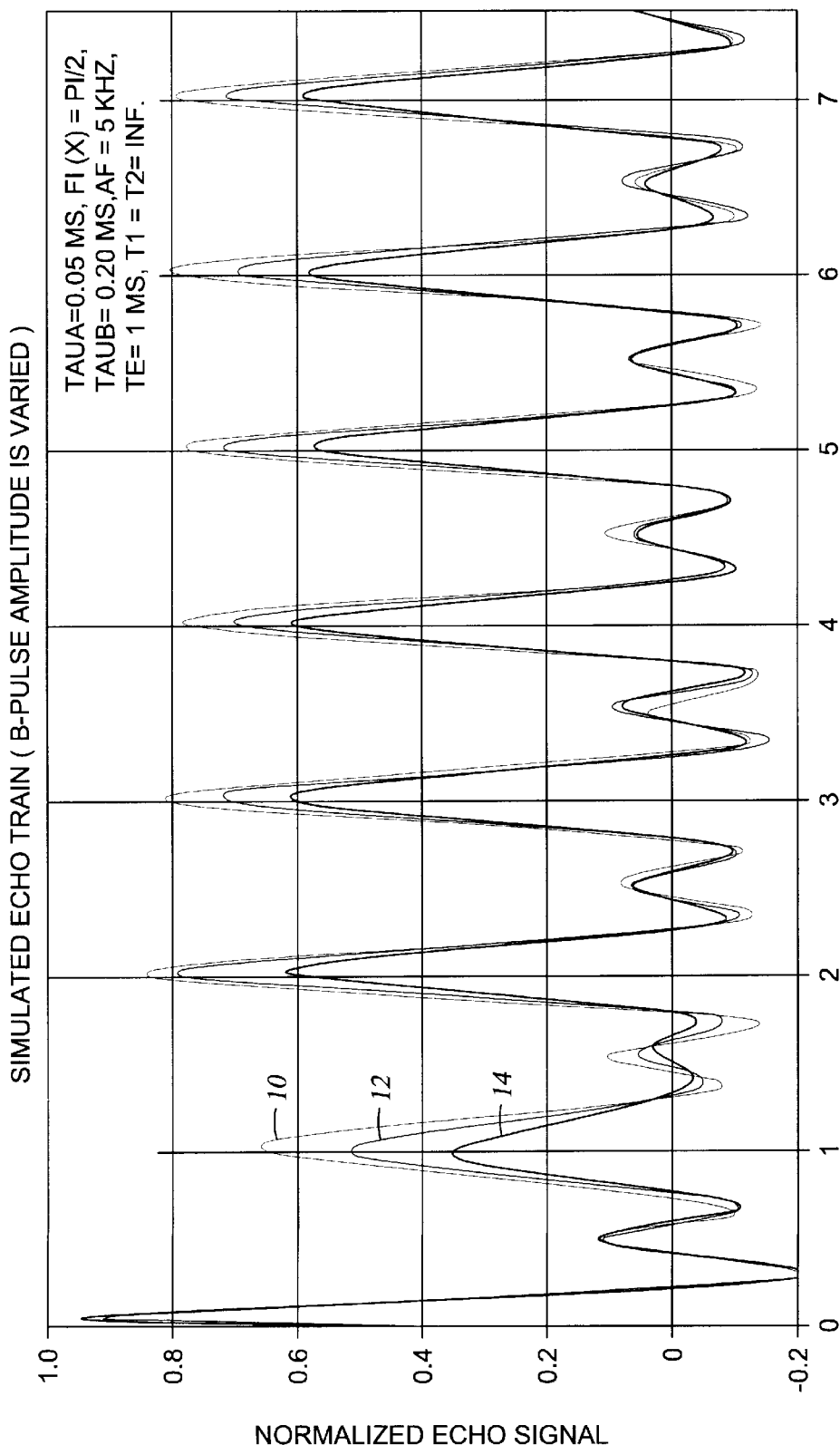
FIG. 1 shows a simulated spin echo train for B-pulse flip angles of 180, 120 and 90 degrees when the flip angle induced by B-pulses is selected by varying the amplitude of the B-pulses.

In the invention, it has been determined that the B-pulses can, and preferably do, have a duration and amplitude selected to cause the nuclear spin axes to reorient by an angular deflection different from 180 degrees. FIG. 1 shows a simulated spin echo "train" (the magnitude of the voltages induced in the receiver coil for each of the spin echoes) for B-pulse angular reorientation (hereafter referred to as the "flip" angle) of 180, 120 and 90 degrees, at curves 10, 12, and 14, respectively. What is apparent from FIG. 1 is that the average amplitude of the spin echoes is reduced only by about 30 percent (although the first and second echoes are reduced in amplitude substantially more than this) by reducing the flip angle of the B-pulses from 180 degrees to 90 degrees.

Reducing the flip angle of the B-pulses from 180 to 90 degrees, however, reduces the amount of electrical power consumed in generating the B-pulses by about 75 percent. The reduction in electric power consumption makes possible generation of additional spin echo measurement sequences using the same overall amount of electrical power. These additional spin echo measurement sequences can be summed or "stacked" to improve the signal to noise ratio ("SNR") over that of a single CPMG sequence using 180 degree B-pulses, while using the same overall amount of electrical power.

For example, four spin echo trains each having a 90 degree flip angle B-pulses could be used, these sequences in total consuming the same overall electrical power as a single spin echo train having 180 degree flip angle B-pulses. The four echo trains can then be stacked. The signal to noise ratio ("SNR") of the four stacked spin echo trains would be twice (square root of four) that of a single spin echo train having 90 degree B-pulses. Four, stacked spin echo trains having 90 degree B-pulses would have SNR about 50 percent more than a single spin echo train having 180 degree B-pulses, owing to the amplitude reduction of the individual spin echoes of about 30 percent for 90 degree B-pulse spin echoes as compared to 180 degree B-pulse spin echoes. The four 90 degree B-pulse echo trains, however, would use about the same amount of electrical power as the single, 180 degree B-pulse sequence. It should be noted that each spin echo train has only one A-pulse, so the A-pulse duration and amplitude do not materially affect the overall electrical power consumption because the typical spin echo train includes about 500 to 1,000 B-pulses, as is known in the art. Another example spin echo train measurement sequence can include stacking only three spin echo trains each having 90 degree B-pulses. This measurement technique would both reduce electrical power consumption and modestly increase overall SNR as compared to a single echo train having 180 degree B-pulses.

Acquiring multiple spin echo trains for summing or stacking can be done in a number of different ways. One way would be to wait for an amount of time between spin echo measurement sequences of about 5 times the T1 value, to allow nuclei in the medium surrounding the instrument to reorient along the static magnetic field. As is understood by those skilled in the art of well logging, waiting for nuclear spin reorientation along the static magnetic field would make the overall measurement technique relatively slow. Therefore, another technique for acquiring multiple measurement sequences for stacking can be performed using an instrument such as one described in U.S. Pat. No. 5,712,566 issued to Taicher et al. The instrument described in the Taicher et al '566 patent can make NMR measurements at a plurality of different radio frequencies. Because the magnet in that instrument induces a static magnetic field having an amplitude gradient, making NMR measurements at different frequencies would cause nuclear magnetic excitation in different excitation volumes. This would eliminate the need to wait between measurement sequences since nuclear reorientation in one excitation volume would not materially affect measurements made in a different excitation volume.

In more general terms, if noise in the measurements is normally distributed, it is possible to determine an optimal flip angle, $\alpha$, for the spin echo train for any given DC (average) by maximizing the value:

$$\frac{180}{\alpha} * \frac{S_\alpha}{S_{180}} \qquad (1)$$

Where $S_{180}$ represents the SNR for the signals acquired using a conventional flip angle of 180 degrees and $S_\alpha$ represents the SNR for the signals acquired using a flip angle $\alpha$. The foregoing description of stacking a number of echo trains to improve SNR while maintaining the same overall power usage is not the only possible way to acquire NMR measurements using the method of this invention. As previously explained, the overall amplitude (and consequently SNR) of the spin echoes in a single echo train using 90 degree B-pulses, for example, is reduced by about 30 percent from a spin echo train using 180 degree B-pulses. However, in the same example, the power used in generating the echo train using 90 degree B-pulses is reduced by about 75 percent from that needed to generate the echo train using 180 degree B-pulses. Using an expression such as that in equation (1), NMR measurements can be made using single echo trains wherein the flip angle is selected to optimize the SNR with respect to the amount of power used to generate the spin echo train. This can result in reduced power usage for a given SNR, or may also allow the system designer to use single echo train measurements wherein the power usage is minimized while maintaining an acceptable SNR for the measurements.

Figure 2:
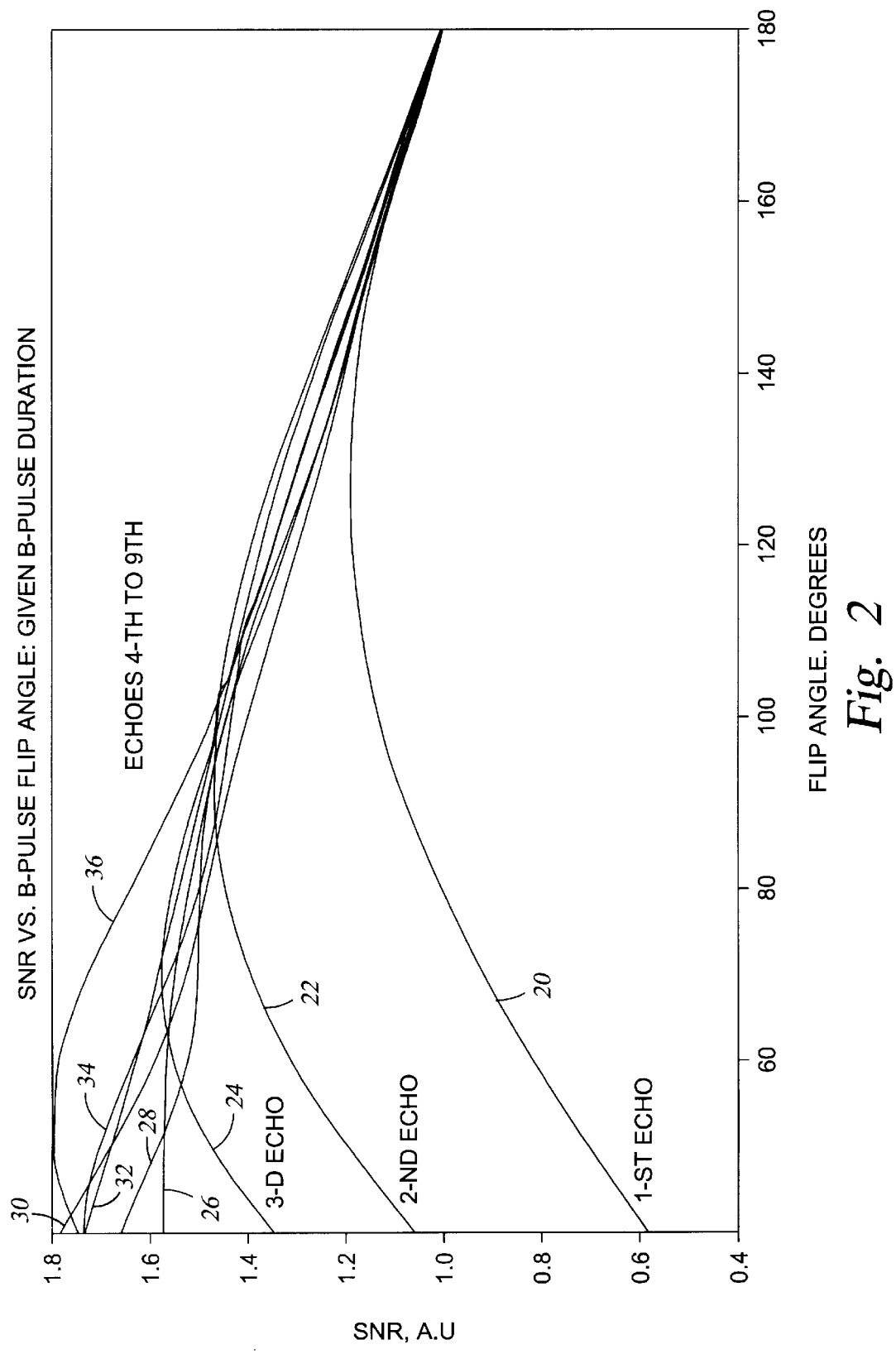
FIG. 2 shows a graph of SNR of "stacked" spin echo trains having varying B-pulse durations, but the same overall power consumption as a single 180 degree B-pulse spin echo train, normalized to the SNR of the single 180 degree B-pulse echo train.

FIG. 2 shows SNR of spin echoes in summed or "stacked" echo trains having varying B-pulse flip angles, the SNR being normalized to the SNR of a single echo train having 180 degree flip angle B-pulses. The number of echo trains stacked for each of the various flip angles is calculated to have the same overall DC power consumption as the single echo train having 180 degree B-pulses. The SNR for some of the individual spin echoes in the "stacked" echo train is shown with respect to the selected B-pulse flip angle. It should be noted that the SNR for these individual echoes represents the stacked value, where the number of these same individually indexed spin echoes in each of the echo trains is equal to the total number of echo trains which is summed. For purposes of calculating the curves shown in FIG. 2, the number of stacked echo trains can be represented by the expression:

$$N = \sqrt{\frac{P_\alpha}{P_{180}}} \qquad (2)$$

where N represents the number of stacked echo trains, $P_\alpha$ represents the power consumed by each spin echo train having B-pulses of flip angle $\alpha$, and $P_{180}$ represents the power consumed by a spin echo train having 180 degree B-pulses. As a practical matter, however, an integral (whole) number of spin echo trains (N) for the selected B-pulse flip angle will most likely stacked for actual spin echo measurements made by a logging instrument in a wellbore.

As can be observed in FIG. 2, for the second through the ninth spin echoes, shown as curves 22 through 36, respectively, the stacked SNR is generally greater than that in a corresponding single echo train having 180 degree B-pulses. As a group, these individual echoes peak in stacked SNR at about 90 to 110 degrees. The first echo, shown at curve 20, is substantially different, having stacked SNR of about 58 percent of a 180 degree spin echo at a flip angle of 40 degrees, with SNR peaking at about 120 to 140 degrees. Using a selection criterion that the stacked first spin echoes should have SNR at least equal to that of a single spin echo train using 180 degree flip angle B-pulses, it can be inferred that B-pulse flip angles in the range of about 80 to 120 degrees will provide substantially improved SNR with respect to an echo train having 180 degree B-pulses, while having the same DC power consumption to generate the B-pulses as that needed to generate a single echo train having 180 degree B-pulses. It should be noted that the graph in FIG. 2 assumes that the particular B-pulse flip angle is selected by selecting the amplitude of the B-pulses. The duration of the B-pulses remains substantially constant. The converse case where the B-pulse amplitude is maintained constant and the duration is varied to select the flip angle will be further explained.

Figure 3:
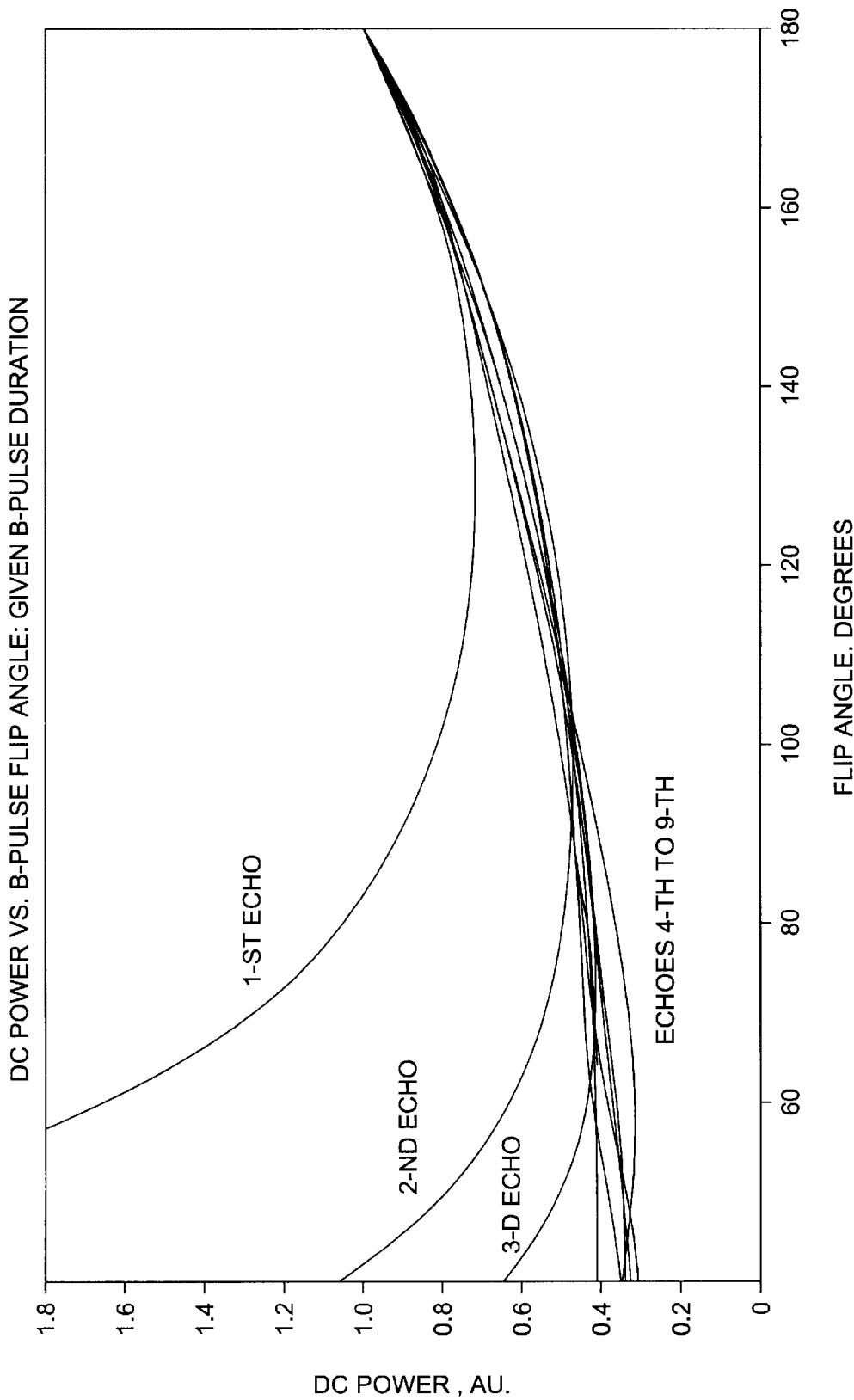
FIG. 3 shows the DC power consumption of the stacked spin echo trains having varying B-pulse durations, but the same SNR, normalized to the power consumption of a single 180 degree B-pulse echo train.

FIG. 3 shows the DC power consumption used in generating B-pulses having the same varying flip angles as shown in FIG. 2, normalized to the DC power consumption used for generating a single 180 degree B-pulse echo train, where the SNR for each of the types of spin echo trains is held substantially constant. The curves for the first to third echoes are shown as 20', 22' and 24', respectively. However, because of the lack of separation between the curves for the fourth to the ninth echoes, these curves are shown as a group identified at 38. Similarly as in the results shown in FIG. 2, for B-pulse flip angles in a range of about 80 to 120 degrees the specific DC power consumption for generating the B-pulses is most reduced from that used to generate B-pulses having a flip angle of 180 degrees.

Figure 4:
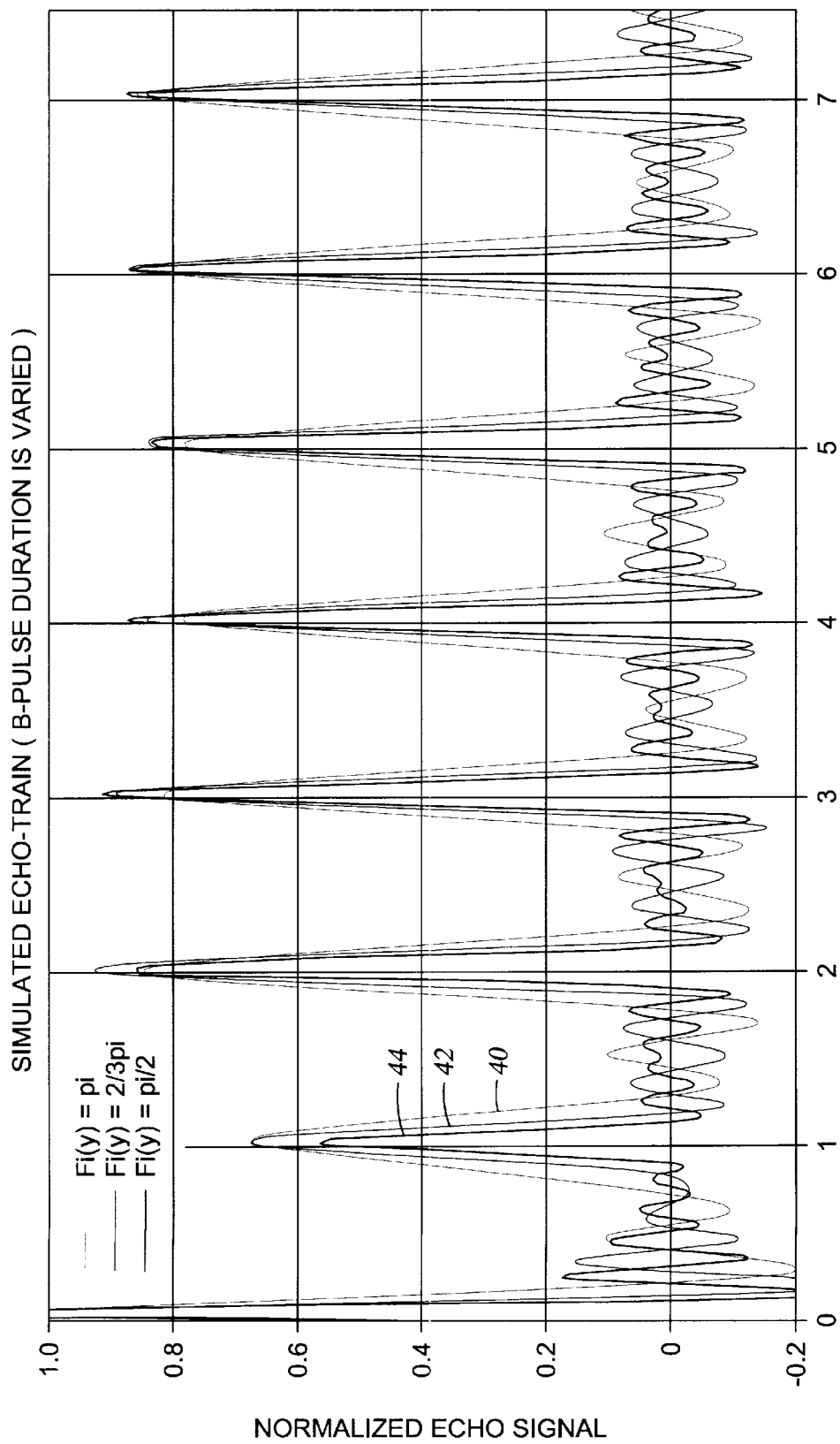
FIG. 4 shows simulated echo trains where the flip angle induced by B-pulses is selected by varying the duration of the B-pulses.
Figure 5:
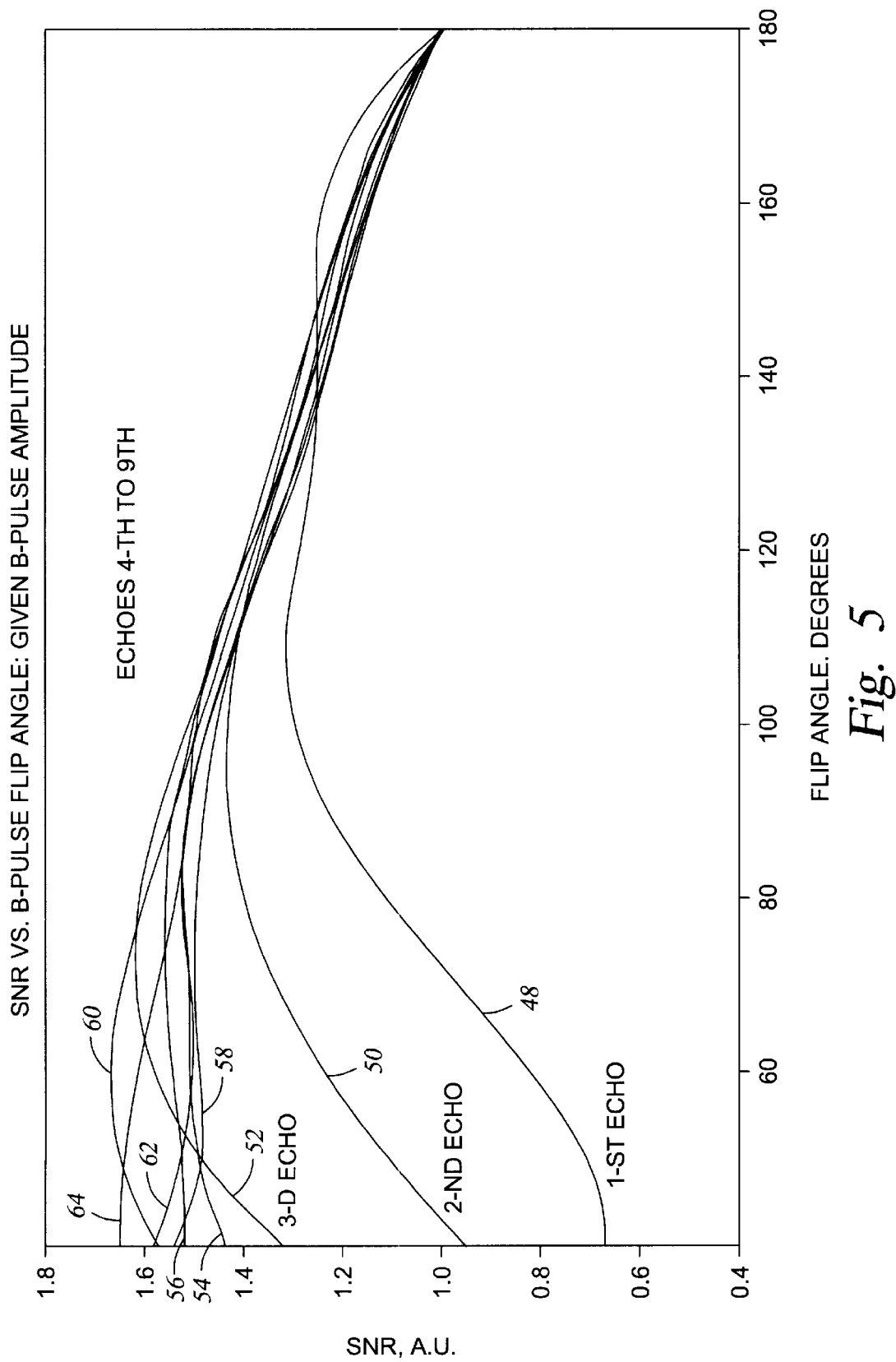
FIG. 5 shows the SNR of stacked echo trains simulated as in FIG. 4 with respect to the flip angle of the B-pulses, normalized to the SNR of a single echo train having a B-pulse flip angle of 180 degrees.

The flip angle induced by the B-pulses can also be selected by varying the duration of the B-pulses while maintaining a substantially constant B-pulse amplitude. An echo train simulation similar to the one shown in FIG. 1 is shown in FIG. 4, where the amplitudes of spin echoes are shown for flip angles of 180 degrees, 120 degrees and 90 degrees at curves 40, 42, and 44, respectively. In the simulation results shown in FIG. 5, the B-pulse flip angle is selected by adjusting the B-pulse duration while maintaining the amplitude substantially constant. Corresponding SNR curves with respect to the B-pulse flip angle are shown in FIG. 5 as curves 48 to 64 for the first echo through ninth echoes respectively. As can be observed in FIG. 5, the SNR for the first echo 48 has a "plateau"-like maximum in a range of about 100 to 160 degrees. The second echo 50 has a peak SNR in the range of about 95–115 degrees. In the graph of FIG. 5, the receiver bandwidth is set to an amount corresponding to the spin echo signal spectrum. In the case of 180, 120 and 90 degree pulses, this bandwidth is 5 kHz, 7.5 kHz and 10 kHz, respectively.

Figure 6:
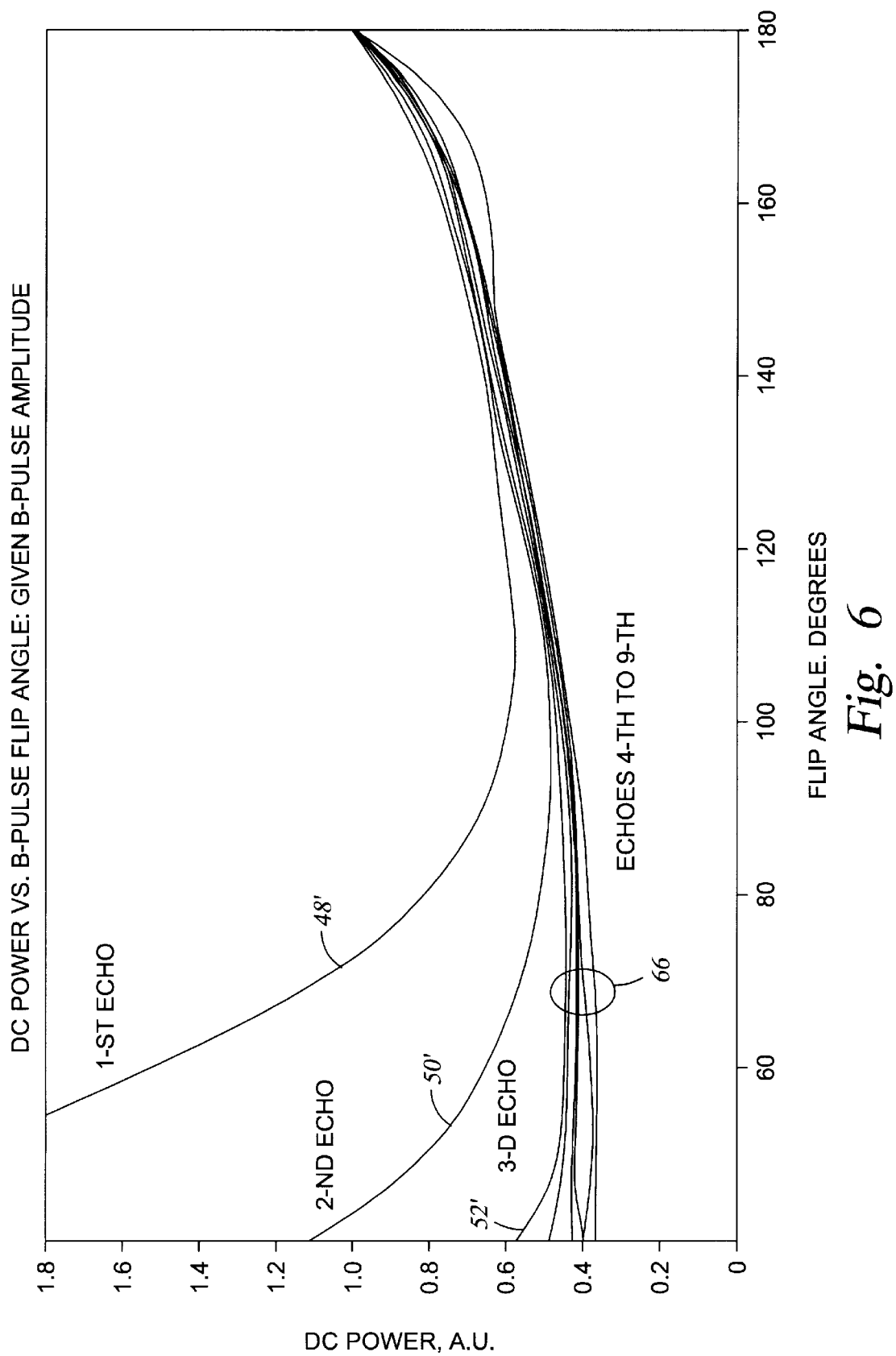
FIG. 6 shows the DC power consumption of the stacked echo trains simulated as in FIG. 4 with respect to the flip angle of the B-pulses, normalized to the DC power consumption of a single echo train having a B-pulse flip angle of 180 degrees.

The DC power consumption normalized to that of 180 degree-duration B-pulses, for the simulated spin echoes shown in FIG. 4, is shown in FIG. 6. The first echo 48 has a minimum power consumption in a range of about 100 to 160 degrees. The second echo 50 has a minimum power consumption in a range of about 95–115 degrees. The second echo pulse is shown by curve 52', while the curves representing the fourth to ninth echoes are shown grouped together at 66.

It should be noted that reducing the B-pulse width to select the flip angle may affect the necessary width of the A-pulse. In conventional NMR spin echo measurements the B-pulses have a duration of about twice that of the A-pulses. If the B-pulse flip angle is reduced by selecting a reduced pulse duration, it may be necessary to correspondingly reduce the A-pulse width (but correspondingly increase the A-pulse amplitude to maintain a 90 degree flip angle) to avoid the situation where the A-pulse does not equally excite all the nuclear magnetic spins which will then be affected by the B-pulses. This effect would spoil any possible signal to noise improvement offered by the method of the invention unless the A-pulse width is reduced to approximately one-half the B-pulse width.

To summarize, using an expression similar to that of equation (1), a B-pulse flip angle can be selected for NMR spin echo measurement sequences which provides a maximum SNR while minimizing the use of electrical power by the instrument.

As is known in the art, NMR well logging measurements as a practical matter are not conducted in a perfectly homogeneous static magnetic field. The NMR signals detected by the typical well logging instrument will therefore have a non-zero bandwidth. A consequence of the bandwidth of the NMR signals is that the spin echo peak amplitudes do not precisely correspond to the theoretical spin echo amplitudes which would obtain for given earth formation properties if the static magnetic field had zero gradient. The magnitude of the effect of signal bandwidth on the spin echo amplitudes is well known. As is known in the art, a correction coefficient can be defined for each spin echo to adjust its amplitude to the theoretical value which would obtain in a zero gradient static magnetic field. This is shown by the following expression:

$$E^c_j = K_j * E^m_j \qquad (3)$$

where $E^c_j$ represents the corrected amplitude of the j-th spin echo, $K_j$ represents the j-th correction factor, and $E^m_j$ represents the j-th measured spin echo amplitude. For the typical NMR well logging instrument, a series of correction factors can be determined for each of the j spin echoes in any measurement sequence. In the case where T1=T2, the values of the correction factors $K_j$ are not dependent on T2. Therefore the same set of correction factors can be used for any set of spin echo measurements when T1=T2.

Figure 7:
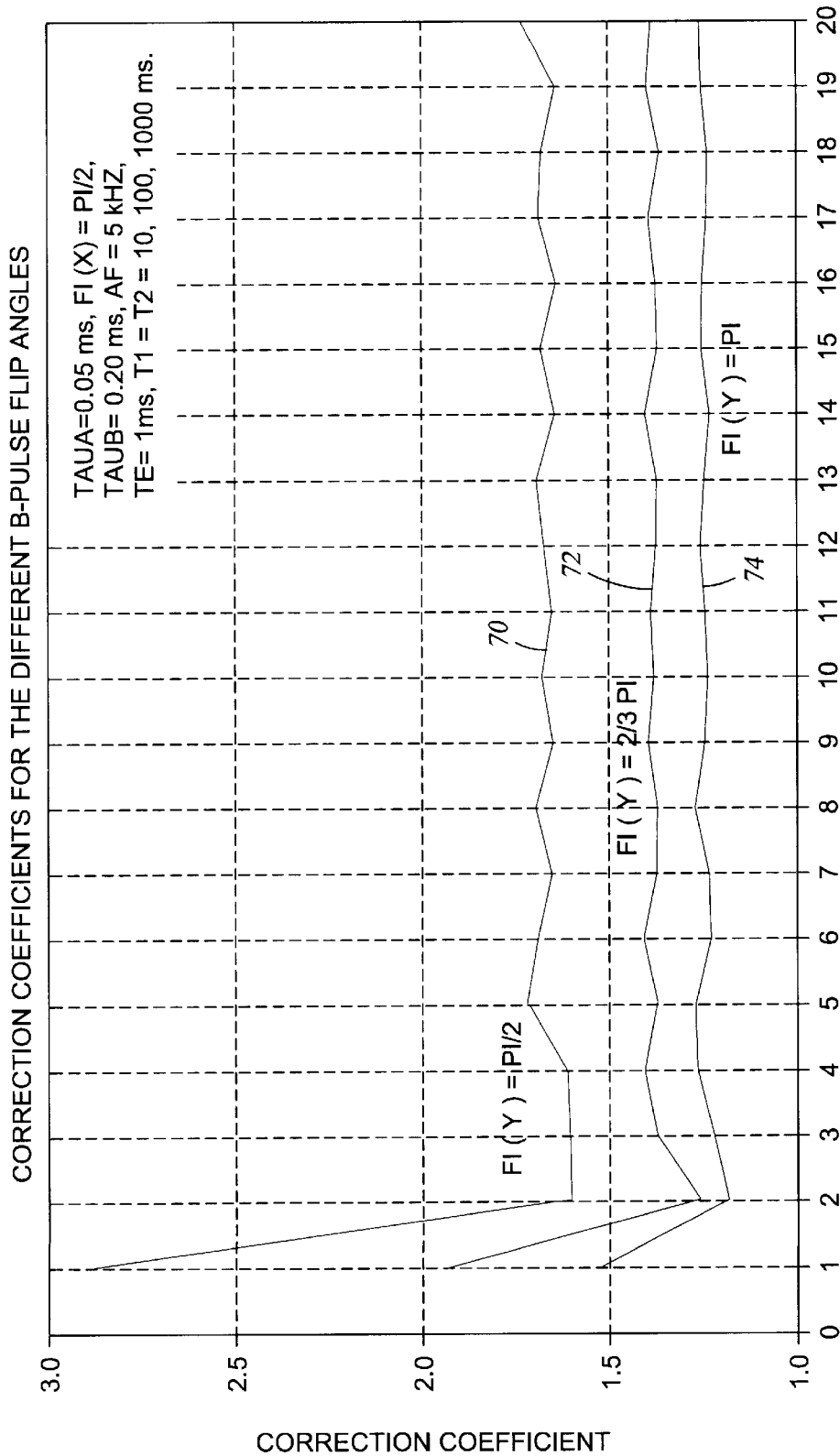
FIG. 7 shows a graph of correction coefficients for each of the first 20 echoes in an echo train for B-pulse flip angles of 180, 120 and 90 degrees, where the value of T2 is selected to be 10, 100 and 1,000 milliseconds for each flip angle.

It has been determined that similar correction factors can be determined for spin echoes in an echo train where the rephasing pulses (B-pulses) have a flip angle other than 90 degrees, which type of echo train is particularly shown in this invention. Referring to FIG. 7, three sets of curves are shown, each set representing the value of the correction factor for particular spin echoes. The value of the correction factor for a B-pulse flip angle is shown in curve set 74. Curve set 74 actually represents three individual curves of correction factor with respect to echo number where the T2 (and T1) value for each individual curve in the set 74 is 10, 100 and 1,000 milliseconds. Set 74 appears as only one curve because the correction factors are essentially independent of T2. Similarly for B-pulse flip angles of 120 degrees, shown in set 72, and 90 degrees, shown in set 70, the values of the correction factors do not change with changes in T2.

The curve sets 70, 72, 74 in FIG. 7 suggest that a different set of correction factors must be determined for each particular value of flip angle, bandwidth and T1/T2 ratio. The values of correction factors are pre calculated just once and can be stored in look up tables, for example, for performing corrections. Therefore this invention does not require any specialized processing as compared to traditional correction procedures where the B-pulse flip angle is 180 degrees.

Those skilled in the art will devise other embodiments of this invention which do not depart from the spirit of the invention as disclosed herein. Accordingly, the invention should be limited in scope only by the attached claims.

What is claimed is:

1. A method for acquiring nuclear magnetic resonance measurements of a material, comprising:

inducing a static magnetic field in said material;

inducing a first radio frequency magnetic field in said material, said first radio frequency magnetic field having an amplitude and duration selected to reorient nuclear magnetic spins in said material by about 90 degrees from alignment with said static magnetic field;

inducing a second radio frequency magnetic field in said material;

detecting nuclear magnetic resonance signals from said material;

repeating said steps of inducing said first and said second radio frequency magnetic fields and detecting said nuclear magnetic resonance signals; and stacking said detected nuclear magnetic resonance signals to form a stacked signal, wherein said second radio frequency magnetic field has a duration and amplitude selected to reorient said nuclear magnetic spins by a flip angle selected so that said stacked signal has increased signal to noise ratio compared to a single nuclear magnetic resonance signal generated wherein said flip angle is 180 degrees, while consuming substantially the same electrical power as used to generate said single nuclear magnetic resonance signal wherein said flip angle is 180 degrees.

2. The method as defined in claim 1 wherein said selected flip angle is determined by adjusting said duration of said second radio frequency magnetic field while maintaining said amplitude of said second radio frequency magnetic field substantially constant.

3. The method as defined in claim 1 wherein said selected angle is determined by adjusting said amplitude of said second radio frequency magnetic field while maintaining said duration of said second radio frequency magnetic field substantially constant.

4. The method as defined in claim 1 wherein said selected angle is in a range of about 80 to 120 degrees.

5. The method as defined in claim 1 wherein each of said steps of inducing said first and said second radio frequency magnetic fields is performed at a different radio frequency and wherein said static magnetic field includes an amplitude gradient within said material, so that each of said steps of inducing said radio frequency magnetic fields and detecting said signals can be performed without waiting for nuclear magnetic reorientation along said static magnetic field of previously radio frequency excited nuclei in said material.

6. A method for acquiring nuclear magnetic resonance measurements of a material, comprising:

inducing a static magnetic field in said material;

inducing a first radio frequency magnetic field in said material, said first radio frequency magnetic field having an amplitude and duration selected to reorient nuclear magnetic spins in said material by about 90 degrees from alignment with said static magnetic field;

inducing a second radio frequency magnetic field in said material;

detecting nuclear magnetic resonance signals from said material;

repeating said steps of inducing said first and said second radio frequency magnetic fields and detecting said nuclear magnetic resonance signals; and stacking said signals from each of said steps of detecting to form a stacked signal, wherein said second radio frequency magnetic field has a duration and amplitude selected to reorient said nuclear magnetic spins by a flip angle selected to provide said stacked signal with substantially the same signal to noise ratio as a single nuclear magnetic resonance signal generated wherein said flip angle is 180 degrees, while consuming less electrical power than used to generate said single signal wherein said flip angle is 180 degrees.

7. The method as defined in claim 6 wherein said selected angle is determined by adjusting said duration of said second power pulses while maintaining said amplitude of said second power pulses substantially constant.

8. The method as defined in claim 6 wherein said selected angle is determined by adjusting said amplitude of said second power pulses while maintaining said duration of said second power pulses substantially constant.

9. The method as defined in claim 6 wherein said selected angle is in a range of about 80 to 120 degrees.

10. The method as defined in claim 6 wherein each of said steps of inducing said first and said second radio frequency magnetic fields is performed at a different radio frequency and wherein said static magnetic field includes an amplitude gradient within said material, so that each of said steps of inducing said radio frequency magnetic fields and detecting said signals can be performed without waiting for nuclear magnetic reorientation along said static magnetic field of previously radio frequency excited nuclei in said material.

11. A method for acquiring nuclear magnetic resonance measurements of a material, and stacking the detected signals comprising:

inducing a static magnetic field in said material;

inducing a first radio frequency magnetic field in said material, said first radio frequency magnetic field having an amplitude and duration selected to reorient nuclear magnetic spins in said material by about 90 degrees from alignment with said static magnetic field; and inducing a plurality of second radio frequency magnetic fields in said material and detecting nuclear magnetic resonance signals from said material, where the detected signals are stacked and said second radio frequency magnetic fields having a duration and amplitude selected to reorient said nuclear magnetic spins by an angle which maximizes signal to noise ratio of said detected signals with respect to an amount of electrical power consumed in generating said second radio frequency magnetic fields.

12. The method as defined in claim 11 wherein said selected flip angle is determined by adjusting said duration of said second radio frequency magnetic fields while maintaining said amplitude of said second radio frequency magnetic field substantially constant.

13. The method as defined in claim 11 wherein said selected angle is determined by adjusting said amplitude of said second radio frequency magnetic fields while maintaining said duration of said second radio frequency magnetic field substantially constant.

14. The method as defined in claim 11 wherein said selected angle is in a range of about 80 to 120 degrees.

* * * * *